United States Patent [19]
Collins

[11] 4,068,530
[45] Jan. 17, 1978

[54] DEVICE AND METHOD FOR OBTAINING ONE OR MORE SAMPLES OF LIQUID

[76] Inventor: William J. Collins, 7005 Madison St., Merrillville, Ind. 46410

[21] Appl. No.: 682,563

[22] Filed: May 3, 1976

Related U.S. Application Data

[62] Division of Ser. No. 543,687, Jan. 24, 1975, Pat. No. 4,002,071.

[51] Int. Cl.² ............................................. G01N 1/12
[52] U.S. Cl. ............................................. 73/425.4 R
[58] Field of Search .................... 73/425.4 R, DIG. 9

[56] References Cited

U.S. PATENT DOCUMENTS

| | | | |
|---|---|---|---|
| 3,415,124 | 12/1968 | Collins | 73/DIG. 9 |
| 3,646,816 | 3/1972 | Hance | 73/DIG. 9 |
| 3,656,350 | 4/1972 | Collins | 73/DIG. 9 |
| 3,791,220 | 2/1974 | Falk | 73/DIG. 9 |
| 3,798,974 | 3/1974 | Boron | 73/DIG. 9 |
| 3,877,309 | 4/1975 | Hance | 73/425.4 R |

*Primary Examiner*—S. Clement Swisher

[57] ABSTRACT

The invention involves providing a device or devices whereby one or more samples of liquid, such as molten metal, may be readily obtained from a mass or stream thereof. More particularly, the device comprises sections forming a chamber, an entrance for receiving molten metal for flow into the chamber and into a pair of tubes extending from the chamber for receiving metal, and a mass of insulation which is disposed in a casing and about the sections and tubes whereby to assist in holding the sections and tubes assembled.

5 Claims, 6 Drawing Figures

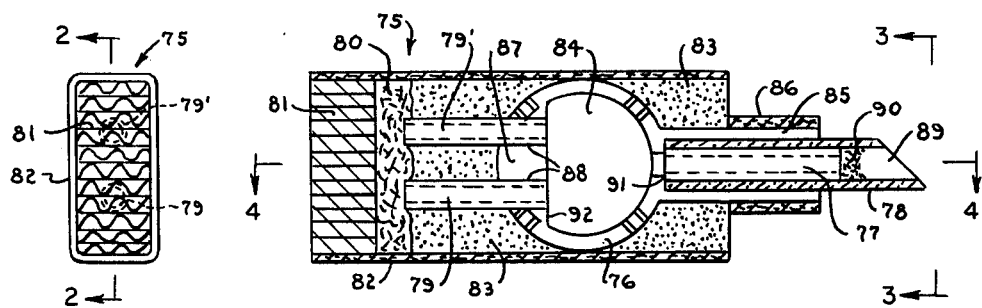
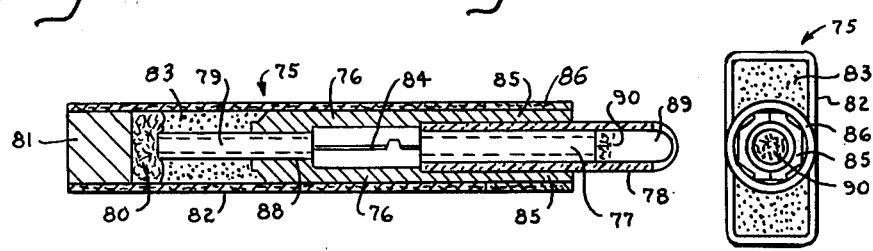

DEVICE AND METHOD FOR OBTAINING ONE OR MORE SAMPLES OF LIQUID

BACKGROUND OF INVENTION

This application is a Division of my copending application Ser. No. 543,687 filed Jan. 24, 1975 now U.S. Pat. No. 4,002,071.

The invention relates to a device and method of extracting one or more samples of molten steel or other types of metal from a stream from the bottom of a ladle. A recognized fact is that the pouring of molten steels or other materials from the bottom of a ladle into the type of cavity or container which it will form; is momentarily exposed to the atmosphere causing a minute but indeterminable amount of contamination from the air. This effects the composition of the steel or other molten metals but is theorized to occur only at the skin or periphery of the molten stream. The stream in effect becomes a column extending from the bottom of a ladle to the top of the point where it begins to become a part of the casting. The teeming in the steel industry may form an ingot, or the metal may be caused to flow into another ladle, a tundish or some other receptacle. Evidence suggests that the techniques used in the steel industry may be applied to other metal industries. The recognition of this contamination makes it desirable to shorten this column length to the minimum giving it as little exposure to the atmosphere as possible. Because of this factor it is believed that the subject invention offers a setup whereby a sample can be more satisfactorily obtained than by other types of devices that have been utilized. It has been observed that by immersing other stream sampling devices directly into the molten column it is difficult to determine the intersection of the tip of the sampling device into the column, whereas crossing the stream laterally by employing a unique connector or holder carried by a lance, staff or wand, affords a clear view of the sampling device and its tangential penetration of the column of steel or other metal. The connector or holder and/or lance facilitates the opportunity of tilting the device at a sharper angle to the stream or molten metal column. Essentially the device can laterally cross the molten metal column from either the right or left, cocking the sampling device to encourage the metal to momentarily penetrate an aperture or entrance provided in a tubulor means constituting a component of the device. The cavity which receives the molten metal substantially freezes it to provide a sample or samples generally similar to those obtained by an immersion type of devices disclosed in my U.S. Pat. No. 3,552,214 dated Jan. 5, 1971.

Another object of the invention is to provide a device in which the wall structure preferably comprises a pair of moulded or formed half sections, each of which includes a relatively large portion provided with a recess and an extended or channel portion, whereby when the sections are correctly assembled the recesses will form the chamber, above referred to, and the channel portions will form a tubular formation which in certain of the devices hereinafter described, receives an inner extremity of a tubular means.

A particular objective is to provide a device whereby samples of different shapes may be obtained, one of which, for example, may include a relatively large portion or head and one or more of which may be in the form of pin portions joined to the head, and the means utilized for obtaining one or more pin portions may also serve as a means for venting a chamber in which the head is formed as generally referred to above.

A specific object of the invention is to provide a device of the character described in the preceeding paragraph in which the means employed to obtain the sample which includes a head comprises the pair of half sections and the means for obtaining one or more pin samples comprises an outlet tube or tubes which are held between the sections and communicate with the chamber, the sections and outlet tubes are preferably imbedded in cement, and a housing or casing surrounds the sections and cement. This modified device also preferably includes a pair of telescoping inlet tubular means or tubes which are operatively associated with one another and the chamber whereby one of the tubular means extends beyond the other to support the latter and promote entry of a fluid into the one, and provide what may be termed a counter-recess or pocket for accommodating a deoxidizing element. The device may also include a plug confined within one end of the housing and filter means located between the plug and the outer ends of the outlet tubes.

Additional objects and advantages of the invention or inventions is to provide a device or structure which are reliable, efficient and comprised of a minimum number of components or parts which can be economically manufactured and assembled on a production basis, all of which is disclosed in the drawings annexed hereto and constitute portions of the subject application.

Referring to the drawings:

FIG. 1 is an end view of a device for obtaining one or more samples of different shapes;

FIG. 2 is a transverse vertical section taken substantially on line 2—2 of FIG. 1;

FIG. 3 is an end view of the device looking in the direction of the arrows 3—3 of FIG. 2;

FIG. 4 is a horizontal section taken substantially on line 4—4 of FIG. 2; and

Figure 5:
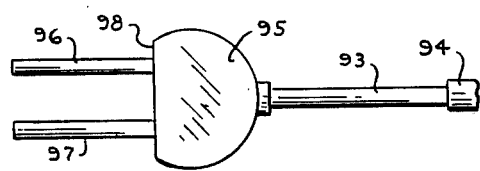
FIGS. 5 and 6 are face and side views of a sample or samples obtained by employing the device shown in FIG. 2.
Figure 6:

FIGS. 1 through 4 depict a device generally designated 75 whereby a sample or joined samples or portions as depicted in FIGS. 5 and 6 may be obtained. More particularly, the device 75 preferably comprises a pair of half sections 76 similar to the half sections of the device 3, an inner inlet tube or tubular means 77, an outer inlet tube or tubular means 78 surrounding the inner tube 77, a pair of corresponding parallel outlet tubes or tubular means 79 and 79 having the same internal diameters, filter means 80, plug means 81, an outer rectangular casing 82 and cement 83 in the casing 82 which substantially surrounds the major portions of the half sections 76 and the outlet tubular means 79 and 79' for maintaining the half sections assembled to form a chamber 84 and all of the tubes or tubular means assembled with the half sections. Obviously, internal cross-dimensions and the lengths of the tubular means 79 and 79' may be different. The half sections include channel or extended portions 85 which form a tubular formation of which a portion thereof extends outwardly from the cement and beyond one end of the casing 82. This formation is surrounded by a short sleeve 86 which assists in holding the channel portions 85 together, including the tubes or tubular means 77 and 78 in a cylindrical opening formed by mating grooves in the channel portions.

The half sections 76 are preferably respectively provided with relatively thick corresponding generally transversely disposed chordal portions 87 (one shown) having mating semi-cylindrical grooves therein. When the sections are assembled these grooves form cylindrical openings which respectively receive inner extremities of the outlet tubular means 79 and 79' so the latter will communicate with the chamber 84. More specifically, the cross-dimensions of the openings formed by the grooves 88 and the tubular means 79 and 79' are preferably such that when the sections are correctly assembled these tubular means are frictionally held therebetween.

The outer ends of the tubular means 79 and 79' preferably extend beyond the cement 83 for disposition in or against the filter means 80. This filter means and the plug means 81 maybe constructed of any material suitable for the purpose. More specifically, the filter means may be steel or fiber glass wool whereby to permit venting of air through the tubular means 79 and 79' into the filter means as the metal flows into the tubular means from the chamber 84, while substantially preventing escape of the metal from the tubular means. The plug means 81 is preferably a laminated unit comprising bonded layers of corrugated pasteboard material extending in planes parallel to the longitudinal axis of the device as shown. It is to be understood that although the outer tubes 79 and 79' are shown in a parallel relationship to the longitudinal axis of the device they may be disposed at oblique or different angles with reference to such axis, or a single tube in lieu of the pair may be located in axially spaced relation to the inlet tubes 77 and 78.

Attention is directed to the important fact that the inlet tubular means or tubes 77 and 78 are preferably constructed of material, such as Pyrex or equivalent relatively inexpensive material as compared to quartz and that they have different lengths and internal diameters. The outer larger and longer tube 78 is bevelled and extends beyond the inner tube 77 to provide what may be termed an entrance recess or pocket 89 within which is contained a conditioning means such as a deoxidizing element 90. The tube 78 serves to support the inner tube 77 and the recess 89 had a cross-dimension greater than the inside diameter of the inner tube whereby to pilot or facilitate entry of molten metal into the inner tube. In other words, the outer tube 78 serves the triple purpose of supporting the inner tube, piloting or guiding the metal into the chamber via the tube 77, and as a receptacle for a deoxidizing element. It should be noted that the half sections are also preferably provided with abutment means 91 (one shown) which serve to limit inward movement of the tubes 77 and 78 during their assembly in the portions 85. It should be manifest that since the channel portions 85 have a length greater than one half the length of the tube 78 it may be stated that the outer extremity of the tube 78 is supported by the channel portions 85.

Attention is also directed to the fact that the device 75 is preferably generally rectangular in cross-section and it is obvious that a connector such as 2, above referred to, may be notched to the correct size, if required, to detachably receive this device. Obviously, this device may have a cross-section other than square or rectangular. The connector is unique since it will accommodate casings which are round, oval, square or rectangular in cross-section.

As alluded to above, FIGS. 5 and 6 depict face and side views of a sample, samples or portions which can be obtained by employing the device 75. More specifically, numeral 93 designates a stem or pin portion formed in the inlet tube 77, 94 a portion formed in the tube 78, 95 an intermediate relatively large portion or head formed in the chamber 84, and pin portions 96 and 97 formed in the outlet tubes 79' and 79. It is to be understood that the designs or shapes shown may be considered to represent a single composite sample or several samples or portions. The pin portions 93, 96 and 97 are preferably disposed with respect to the intermediate or head portion 95 so that any one or all of the portions may be separated and utilized for analysis. It should be noted that the portion 95 has a uniform thickness which is greater than the cross-dimensions of the other portions and is substantially round except for its chordal marginal edge 98. It is to be understood that the cross-dimension and length of the various portions may be modified by changing the dimensions of the chamber and tubular means of the device.

Summarizing the above in a general way it is to be understood that the device described is capable of being readily detachably connected to a lance through the agency of a connector, such as 2 as described in the parent application; that the device 75 offers a setup whereby several sample portions of predetermined shapes may be readily obtained for analysis; that tubular means or structure of the same or different diameters and lengths may be utilized to obtain sample portions of predetermined shapes, sizes or weights; that the device is preferably adapted for attachment to a lance in a position substantially transverse thereto whereby to promote safety since an operator is offered many standing positions with respect to a stream of molten metal to better view the penetration of the entrance end of the device into the stream; that the device is constructed and arranged for manufacture on a production basis; and that the outer casing of the device may be considered to constitute a handle, grip or component which is received in a connector.

Attention is directed to the fact that bevelled entrances of the tubular means of all of the devices are preferably disposed in a predetermined position with respect to the primary chambers or receiving means, so that when any device is being so used its chamber will generally be in a substantially vertical plane and this will allow the molten metal to flow initially downwardly as it enters the chamber.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. Structure constituting a subassembly of a device for obtaining a sample of molten material, said subassembly comprising a pair of half sections, each of said sections having a head provided with a recess and an extended portion provided with a groove, said head of each section also having a relatively thick portion provided with a pair of grooves spaced from the grooves in the extended portions, the arrangement being such that when the sections are correctly assembled, said recesses and grooves in said extended portions will form a primary chamber and an opening leading thereto and said grooves in said thick portions will form a pair of openings, a pair of tubular means secured in said last mentioned openings and providing secondary chambers for receiving molten material from said primary chamber, and a pair of telescopically engaged refractory tubes secured in said opening formed by said extended portions with one tube being extended in advance of the other for initially receiving molten material for flow into said primary chamber.

2. The structure defined in claim 3, including a third tubular means secured about said extended portions, said pair of tubular means has extremities extending away from said heads, and means of a material different from said sections for substantially surrounding and supporting said extremities.

3. A device for obtaining a sample of molten material, said device comprising, an elongated casing, structure disposed in said casing and forming a primary chamber having an entrance for receiving such material for solidification in said chamber, a pair of tubular means secured to said structure providing a pair of secondary chambers spaced from said entrance for receiving the material from said primary chamber for solidification whereby to obtain a sample having a large portion formed in the primary chamber and a pair of smaller portions extending from said large portion in a direction away from said entrance, and insulating material disposed in and engaging said casing and substantially surrounding and engaging said tubular means for fixedly securing them in relation to said structure and said casing.

4. A device for obtaining a sample of molten material, said device comprising an elongated casing, structure disposed in said casing having an enlargement forming a primary chamber and also having a tubular exposed entrance for initially receiving such material for flow into said chamber, said structure also comprising a pair of separate tubular means forming a pair of secondary chambers communicatively connected to said primary chamber, means in said casing serving to substantially prevent the outflow of the material from said secondary chambers, said primary and secondary chambers serving when the material solidifies therein to form a sample having a large portion and a pair of smaller portions extending from said large portion in a direction from said tubular entrance, and solidified insulating means substantially surrounding said enlargement and held in place by said casing.

5. The device defined in claim 4, in which said casing is non-circular in cross-section and said insulating means substantially engages and conforms to the cross-sectional shape of said casing.

* * * * *